(12) United States Patent
Ayscough et al.

(10) Patent No.: US 6,306,881 B1
(45) Date of Patent: Oct. 23, 2001

(54) ANTI-INFLAMMATORY AGENTS

(75) Inventors: Andrew Paul Ayscough; Mark Whittaker, both of Cowley (GB)

(73) Assignee: British Biotech Pharmaceuticals, Oxford (GB)

( * ) Notice: Subject to any disclaimer, the term of this patent is extended or adjusted under 35 U.S.C. 154(b) by 0 days.

(21) Appl. No.: 09/341,929

(22) PCT Filed: Jan. 27, 1999

(86) PCT No.: PCT/GB99/00284

§ 371 Date: Jul. 21, 1999

§ 102(e) Date: Jul. 21, 1999

(30) Foreign Application Priority Data

Feb. 12, 1998 (GB) .................................................. 9803005

(51) Int. Cl.⁷ ........................ A61K 31/215; A61K 31/22
(52) U.S. Cl. .................... 514/327; 514/438; 514/445; 514/542; 514/551; 546/221; 549/65; 549/76; 560/41; 560/169
(58) Field of Search ........................ 546/221; 549/65, 549/76; 560/41, 169; 514/327, 438, 445, 542, 551

(56) References Cited

FOREIGN PATENT DOCUMENTS

| 0 082 088 B1 | 4/1986 | (EP) . |
| 0 423 943 A2 | 4/1991 | (EP) . |
| 0 489 577 B1 | 3/1995 | (EP) . |
| 0 489 579 B1 | 3/1995 | (EP) . |
| WO 92/09563 | 6/1992 | (WO) . |
| WO 93/24449 | 12/1993 | (WO) . |
| WO 94/25434 | 11/1994 | (WO) . |
| WO 94/25435 | 11/1994 | (WO) . |
| WO 95/04033 | 2/1995 | (WO) . |
| WO 95/19965 | 7/1995 | (WO) . |
| WO 95/22966 | 8/1995 | (WO) . |
| WO 96/33166 | 10/1996 | (WO) . |
| WO 97/49674 | 12/1997 | (WO) . |
| WO 98/11063 | 3/1998 | (WO) . |
| WO 93/09097 | 5/1998 | (WO) . |

OTHER PUBLICATIONS

Bauer et al., Tetra. Lett., 1997, 38, 7233–7236.
E. Bourdel et al., Int. J. Peptide and Protein Rsch., 1996, 48, 148–155.
T.D. Penning et al., Biorg. Med. Chem. Lett., 1995, 5, 2517–2522.
M. Q. Zhang, Curr. Med. Chem., 1994, 4, 67–78.
R.A. Lewis et al., N. Engl. J. Med., 1990, 323, 645–655.

*Primary Examiner*—Richard L. Raymond
(74) *Attorney, Agent, or Firm*—Greenberg Traurig LLP

(57) ABSTRACT

Compounds of general formula (I)

(I)

wherein $R_4$ is an ester or thioester group and R, $R_1$, $R_2$, and $R_3$ are as specified in the description, inhibit intracellular Leukotriene $A_4$ hydrolase activity and are therefore of value for the treatment of inflammatory disease.

15 Claims, No Drawings

ANTI-INFLAMMATORY AGENTS

This application is a 371 of PCT/GB99/00284, filed Jan. 27, 1999.

The present invention relates to the use of certain esters and thioesters for the treatment of diseases responsive to inhibition of intracellular leukotriene-$A_4$ hydrolase activity.

BACKGROUND TO THE INVENTION

The leukotriene cascade of arachadonic acid is a key mechanism in many inflammatory and allergic disease states. The dihydroxy fatty acid leukotriene $B_4$ ($LTB_4$), produced by this cascade, is a key pro-inflammatory mediator. $LTB_4$ stimulates adhesion of circulating neutrophils to vascular endothelium, directs their migration toward sites of inflammation, and induces secretion of further inflammatory mediators. (For reviews see R. A. Lewis et al, N. Engl. J. Med. 1990, 323, 645–655 and M. -Q. Zhang, Curr. Med. Chem. 1997, 4, 67–78.) Leukotriene-$A_4$ hydrolase ($LTA_4$-hydrolase) (EC 3.3.2.6) is an enzyme that catalyses the final and rate limiting step in the synthesis of $LTB_4$. Inhibition of $LTA_4$ hydrolase selectively blocks the biosynthesis of $LTB_4$ which may provide an advantage over current inhibitors, such as those of 5-lipoxygenase, that block earlier in the leukotriene cascade and as a result are less selective.

Disease states associated with elevated levels of $LTB_4$, and which are therefore considered to be responsive to inhibition of intracellular leukotriene-$A_4$ hydrolase activity include asthma, inflammatory bowel disease, psoriasis and arthritis.

Peptidomimetic compounds, such as bestatin, captopril and kelatorphan exhibit $LTA_4$ hydrolase inhibitory activity against isolated enzyme (T. D. Penning et al, Biorg. Med. Chem. Lett., 1995, 5, p2517–2522). However, these compounds are unable to effectively penetrate cells and hence have little anti-inflammatory activity. There is therefore a need in the art for compounds which are capable of inhibiting intracellular $LTA_4$ hydrolase activity.

BRIEF DESCRIPTION OF THE INVENTION

This invention is based on the finding that certain esters and thioesters are capable of inhibiting intracellular $LTA_4$ hydrolase activity, resulting in attenuation of $LTB_4$ biosynthesis. Those esters and thioesters are therefore of use for the treatment of diseases responsive to such inhibiton, for example inflammatory and allergic conditions including asthma, rheumatoid arthritis, osteoarthritis, ulcerative colitis, contact and atopic dermatitis, psoriasis, inflammatory bowel disease and Crohn's disease.

In our earlier international patent application PCT/GB97/02398 (WO 98/11063), there is disclosed the use of the same class of esters and thioesters as inhibitors of the proliferation of rapidly dividing cells, and thus as agents for the treatment, inter alia, of cancer. However, the present utility as inhibitors of $LTA_4$ hydrolase is unrelated to and not predictable from the teaching of that application.

A few patent publications (WO 92/09563, U.S. Pat. No. 5,183,900, U.S. Pat. No. 5,270,326, EP-A-0489577, EP-A-0489579, WO 93/09097, WO 93/24449, WO 94/25434, WO 94/25435, WO 95/04033, WO 95/19965, and WO 95/22966) include within their generic disclosure carboxylate ester compounds having matrix metalloproteinase inhibitory activity. In accordance with the present invention, such compounds are now recognised to have $LTA_4$ hydrolase activity, but that activity is not suggested by, or predictable from, those publications.

WO 95/04033 discloses $N^4$-hydroxy-$N^1$-(1-(S)-methoxycarbonyl-2,2-dimethylpropyl)-2-(R)-(4-chlorophenylpropyl)succinamide as an intermediate for the preparation of the corresponding methylamide MMP inhibitor. In addition, Int. J. Pept. Protein Res. (1996), 48(2). 148–155 discloses the compound

as an intermediate in the preparation of compounds which are inhibitors of neurotensin-degrading enzymes. However, those two appear to be the only specific known carboxylate ester compounds of the kind with which this invention is concerned.

DETAILED DESCRIPTION OF THE INVENTION

In its broadest aspect, the present invention provides a method for treatment of mammals suffering diseases responsive to inhibition of intracellular leukotriene-$A_4$ hydroiase activity, comprising administering to the mammal suffering such disease an amount of a compound of general formula (I) or a pharmaceutically acceptable salt hydrate or solvate thereof sufficient to inhibit such activity:

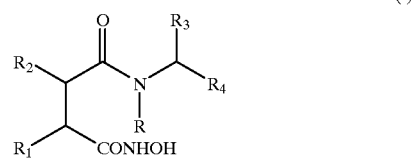

(I)

wherein
R is hydrogen or ($C_1$–$C_6$)alkyl;
$R_1$ is hydrogen;
($C_1$–$C_6$)alkyl;
($C_2$–$C_6$)alkenyl;
phenyl or substituted phenyl;
phenyl ($C_1$–$C_6$)alkyl or substituted phenyl($C_1$–$C_6$)alkyl;
phenyl ($C_2$–$C_6$)alkenyl or substituted phenyl($C_2$–$C_6$)alkenyl
heterocyclyl or substituted heterocyclyl;
heterocyclyl($C_1$–$C_6$)alkyl or substituted heterocyclyl ($C_1$–$C_6$)alkyl;
a group $BSO_nA$- wherein n is 0, 1 or 2 and B is hydrogen or a ($C_1$–$C_6$) alkyl, phenyl, substituted phenyl, heterocyclyl substituted heterocyclyl, ($C_1$–$C_6$)alkyl, phenacyl or substituted phenacyl group, and A represents ($C_1$–$C_6$)alkylene;
hydroxy or ($C_1$–$C_6$)alkoxy;
amino, protected amino, acylamino, ($C_1$–$C_6$) alkylamino or di-($C_1$–$C_6$)alkylamino;
mercapto or ($C_1$–$C_6$)alkylthio;
amino($C_1$–$C_6$)alkyl, ($C_1$–$C_6$)alkylamino($C_1$–$C_6$)alkyl, di($C_1$–$C_6$)alkylamino($C_1$–$C_6$)alkyl, hydroxy($C_1$–$C_6$) alkyl, mercapto($C_1$–$C_6$)alkyl or carboxy($C_1$–$C_6$) alkyl wherein the amino-, hydroxy-, mercapto- or carboxyl-group are optionally protected or the carboxyl-group amidated;
lower alkyl substituted by carbamoyl, mono($C_1$–$C_6$alkyl)carbamoyl, di($C_1$–$C_6$alkyl)carbamoyl, di($C_1$–$C_6$alkyl)amino, or carboxy-$C_1$–$C_6$alkanoylamino; or
a cycloalkyl, cycloalkenyl or non-aromatic heterocyclic ring containing up to 3 heteroatoms, any of which may be (i) substituted by one or more substituents selected from $C_1$–$C_6$ alkyl, $C_2$–$C_6$ alkenyl, halo, cyano (—CN), —$CO_2H$, —$CO_2R$, —$CONH_2$, —CONHR, —CON(R)$_2$, —OH, —OR, oxo-, —SH, —SR, —NHCOR, and —NHCO$_2$R wherein R is $C_1$–$C_6$ alkyl or benzyl and/or (ii) fused to a cycloalkyl or heterocyclic ring;

$R_2$ is a $C_1$–$C_{12}$ alkyl,
$C_2$–$C_{12}$ alkenyl,
$C_2$–$C_{12}$ alkynyl,
phenyl($C_1$–$C_6$ alkyl)-,
heteroaryl($C_1$–$C_6$ alkyl)-,
phenyl($C_2$–$C_6$ alkenyl)-,
heteroaryl($C_2$–$C_6$ alkenyl)-,
phenyl($C_2$–$C_6$ alkynyl)-,
heteroaryl($C_2$–$C_6$ alkynyl)-,
cycloalkyl($C_1$–$C_6$ alkyl)-,
cycloalkyl($C_2$–$C_6$ alkenyl)-,
cycloalkyl($C_2$–$C_6$ alkynyl)-,
cycloalkenyl($C_1$–$C_6$ alkyl)-,
cycloalkenyl($C_2$–$C_6$ alkenyl)-,
cycloalkenyl($C_2$–$C_6$ alkynyl)-,
phenyl($C_1$–$C_6$ alkyl)O($C_1$–$C_6$ alkyl)-, or
heteroaryl($C_1$–$C_6$ alkyl)O($C_1$–$C_6$ alkyl)- group,
any one of which may be optionally substituted by
$C_1$–$C_6$ alkyl,
$C_1$–$C_6$ alkoxy,
halo, or
cyano (—CN);
phenyl or heteroaryl, or
phenyl or heteroaryl substituted by
$C_1$–$C_6$ alkyl,
$C_1$–$C_6$ alkoxy,
halo, or
cyano (—CN);

$R_3$ is the characterising group of a natural or non-natural α amino acid in which any functional groups may be protected; and $R_4$ is an ester or thioester group,
or a pharmaceutically acceptable salt, hydrate or solvate thereof.

In another broad aspect of the invention, there is provided the use of a compound of formula (I) as defined in the immediately preceding paragraph, in the preparation of a pharmaceutical composition treatment of mammals suffering diseases responsive to inhibition of intracellular leukotriene-$A_4$ hydrolase activity, In one particular aspect of the invention, the compound used is one of general formula (I) above wherein R, $R_1$, $R_2$, $R_3$ and $R_4$ are as defined above with reference to formula (I), or a pharmaceutically acceptable salt, hydrate or solvate thereof, PROVIDED THAT:
(i) when R and $R_1$ are hydrogen, $R_2$ is 4-chlorophenylpropyl, and $R^3$ is tertbutyl, then $R_4$ is not a methyl carboxylate ester group; and
(ii) when R and $R_1$ are hydrogen, $R_2$ is phenylmethyl, and $R^3$ is 1-methylprop-1-yl, then $R_4$ is not a tert-butyl carboxylate ester group.

In another particular aspect of the invention, the compound used is one of general formula (I) above wherein:
R, $R_1$ and $R_4$ are as defined above with reference to formula (I)
$R_2$ is $C_1$–$C_{12}$ alkyl, $C_2$–$C_2$ alkenyl, $C_2$–$C_{12}$ alkynyl, biphenyl($C_1$–$C_6$ alkyl)-, phenylheteroaryl($C_1$–$C_6$ alkyl)-, heteroarylphenyl($C_1$–$C_6$ alkyl)-,
biphenyl($C_2$–$C_6$ alkenyl)-, phenylheteroaryl($C_2$–$C_6$ alkenyl)-, heteroarylphenyl($C_2$–$C_6$ alkenyl)-,
phenyl($C_2$–C6 alkynyl)-, heteroaryl($C_2$–$C_6$ alkynyl)-,
biphenyl($C_2$–$C_6$ alkynyl)-, phenylheteroaryl($C_2$–$C_6$ alkynyl)-,
heteroarylphenyl($C_2$–$C_6$ alkynyl)-,
phenyl($C_1$–$C_6$ alkyl)O($C_1$–$C_6$ alkyl)-, or heteroaryl ($C_1$–$C_6$ alkyl)O($C_1$–$C_6$ alkyl)-,
any one of which may be optionally substituted on a ring carbon atom by $C_1$–$C_6$ alkyl, $C_1$–$C_6$ alkoxy, halo, or cyano (—CN); and $R_3$ is $C_1$–$C_6$ alkyl, optionally substituted benzyl, optionally substituted phenyl, optionally substituted heteroaryl; or
the characterising group of a natural α amino acid, in which any functional group may be protected, any amino group may be acylated and any carboxyl group present may be amidated; or
a heterocyclic($C_1$–$C_6$)alkyl group, optionally substituted in the heterocyclic ring;
or a pharmaceutically acceptable salt, hydrate or solvate thereof.

As used herein the term "($C_1$–$C_6$)alkyl" or "lower alkyl" means a straight or branched chain alkyl moiety having from 1 to 6 carbon atoms, including for example, methyl, ethyl, n-propyl, isopropyl, n-butyl, isobutyl, sec-butyl, t-butyl, n-pentyl and n-hexyl.

The term "($C_2$–$C_6$)alkenyl" means a straight or branched chain alkenyl moiety having from 2 to 6 carbon atoms having at least one double bond of either E or Z stereochemistry where applicable. This term would include, for example, vinyl, allyl, 1- and 2-butenyl and 2-methyl-2-propenyl.

The term "$C_2$–$C_6$ alkynyl" refers to straight chain or branched chain hydrocarbon groups having from two to six carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

The term "cycloalkyl" means a saturated alicyclic moiety having from 3–8 carbon atoms and includes, for example, cyclohexyl, cyclooctyl, cycloheptyl, cyclopentyl, cyclobutyl and cyclopropyl.

The term "cycloalkenyl" means an unsaturated alicyclic moiety having from 4–8 carbon atoms and includes, for example, cyclohexenyl, cyclooctenyl, cycloheptenyl, cyclopentenyl, and cyclobutenyl. In the case of cycloalkenyl rings of from 5–8 carbon atoms, the ring may contain more than one double bond.

The term "aryl" means an unsaturated aromatic carbocyclic group which is moncyclic (eg phenyl) or polycyclic (eg naphthyl).

The unqualified term "heterocyclyl" or "heterocyclic" means (i) a 5–7 membered heterocyclic ring containing one or more heteroatoms selected from S, N and O, and optionally fused to a benzene ring, including for example, pyrrolyl, furyl, thienyl, piperidinyl, imidazolyl, oxazolyl, thiazolyl, thiadiazolyl, pyrazolyl, pyridinyl. pyrrolidinyl, pyrimidinyl, morpholinyl, piperazinyl, indolyl, benzimidazolyl, maleimido, succinimido, phthalimido, 1,2-dimethyl-3,5-dioxo-1,2,4-triazolidin-4-yl, 3,4,4-trimethyl-2,5-dioxo-1-imidazolidinyl, 2-methyl-3,5-dioxo-1,2,4-oxadiazol4-yl, 3-methyl-2,4,5-trioxo-1-imidazolidinyl, 2,5-dioxo-3-phenyl-1-imidazolidinyl, 2-oxo-1-pyrrolidinyl, 2,5-dioxo-1-pyrrolidinyl or 2,6-dioxopiperidinyl, or (ii) a naphththal-imido (ie 1,3-dihydro-1,3-dioxo-2H-benz[f]isoindol-2-yl), 1,3-dihydro-1-oxo-2H-benz[f]isoindol-2-yl, 1,3-dihydro-1, 3-dioxo-2H-pyrrolo[3,4-b]quinolin-2-yl, or 2,3-dihydro-1, 3-dioxo-1H-benz[d,e]isoquinolin-2-yl group.

The term "heteroaryl" means a 5–7 membered substituted or unsubstituted aromatic heterocycle containing one or more heteroatoms. Illustrative of such rings are thienyl, furyl, pyrrolyl, imidazolyl, thiazolyl, pyrazolyl, isoxazolyl, isothiazolyl, trizolyl, thiadiazolyl, oxadiazolyl, pyridinyl, pyridazinyl, pyrimidinyl, pyrazinyl and triazinyl.

The term "ester" or "esterified carboxyl group" means a group $R_9O(C=O)$— in which $R_9$ is the group characterising the ester, notionally derived from the alcohol $R_9OH$.

The term "thioester" means a group $R_9S(C=O)$— or $R_9S(C=S)$— or $R_9O(C=S)$—in which $R_9$ is the group characterising the thioester, notionally derived from the alcohol $R_9OH$ or the thioalcohol $R_9SH$.

Unless otherwise specified in the context in which it occurs, the term "substituted" as applied to any moiety herein means substituted with up to four substituents, each of which independently may be ($C_1$–$C_6$)alkyl, ($C_1$–$C_6$) alkoxy, hydroxy, mercapto, ($C_1$–$C_6$)alkylthio, amino, halo (including fluoro, chloro, bromo and iodo), nitro, trifluoromethyl, —COOH, —CONH$_2$, —CN, —COOR$^A$, —CONHR$^A$ or —CONHR$^A$R$^A$ wherein R$^A$ is a ($C_1$–$C_6$) alkyl group or the residue of a natural alpha-amino acid.

The term "side chain of a natural or non-natural alpha-amino acid" means the group $R^1$ in a natural or non-natural amino acid of formula NH$_2$—CH(R$^1$)—COOH.

Examples of side chains of natural alpha amino acids include those of alanine, arginine, asparagine, aspartic acid, cysteine, cystine, glutamic acid, histidine, 5-hydroxylysine, 4-hydroxyproline, isoleucine, leucine, lysine, methionine, phenylalanine, proline, serine, threonine, tryptophan, tyrosine, valine, α-aminoadipic acid, α-amino-n-butyric acid, 3,4-dihydroxyphenylalanine, homoserine, α-methylserine, ornithine, pipecolic acid, and thyroxine.

Natural alpha-amino acids which contain functional substituents, for example amino, carboxyl, hydroxy, mercapto, guanidyl, imidazolyl, or indolyl groups in their characteristic side chains include arginine, lysine, glutamic acid, aspartic acid, tryptophan, histidine, serine, threonine, tyrosine, and cysteine. When $R_3$ in the compounds of the invention is one of those side chains, the functional substituent may optionally be protected.

The term "protected" when used in relation to a functional substituent in a side chain of a natural alpha-amino acid means a derivative of such a substituent which is substantially non-functional. For example, carboxyl groups may be esterified (for example as a $C_1$–$C_6$ alkyl ester), amino groups may be converted to amides (for example as a NHCOC$_1$–$C_6$ alkyl amide) or carbamates (for example as an NHC(=O) OC$_1$–$C_6$ alkyl or NHC(=O)OCH$_2$Ph carbamate), hydroxyl groups may be converted to ethers (for example an OC$_1$–$C_6$ alkyl or a O($C_1$–$C_6$ alkyl)phenyl ether) or esters (for example a OC(=O)$C_1$–$C_6$ alkyl ester) and thiol groups may be converted to thioethers (for example a tert-butyl or benzyl thioether) or thioesters (for example a SC(=O)$C_1$–$C_6$ alkyl thioester).

Examples of side chains of non-natural alpha amino acids include those referred to below in the discussion of suitable $R_3$ groups for use in compounds of the present invention.

Salts of the compounds used in the invention include physiologically acceptable acid addition salts for example hydrochlorides, hydrobromides, sulphates, methane sulphonates, p-toluenesulphonates, phosphates, acetates, citrates, succinates, lactates, tartrates, fumarates and maleates. Salts may also be formed with bases, for example sodium, potassium, magnesium, and calcium salts.

There are several chiral centres in the compounds used according to the invention because of the presence of asymmetric carbon atoms. The presence of several asymmetric carbon atoms gives rise to a number of diastereomers with R or S stereochemistry at each chiral centre. For example, in the compounds used in the invention, the C atom carrying the hydroxamic acid and $R_1$ groups may be in the R or S configuration, the C atom carrying the $R_2$ group may be predominantly in the R configuration, and the C atom carrying the $R_3$ and $R_4$ groups may be in either the R or S configuration, with the predominantly S configuration presently preferred.

As mentioned above, compounds of formula (I) above, and those of formula (i) excluded by the provisos in the definition of formula (I) above, are useful in human or veterinary medicine since they are inhibitors of intracellular leukotriene-A$_4$ hydrolase activity. The utility of the invention therefore lies in the treatment of inflammatory and alergic conditions, such as asthma, rheumatoid arthritis, osteoarthritis, ulcerative colitis, contact and atopic dermatitis, psoriasis, multiple sclerosis, inflammatory bowel disease and Crohn's disease.

The compounds with which the invention is concerned may be prepared for administration by any route consistent with their pharmacokinetic properties.

Orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment Cream or ointment formulations which may be used for the drug are conventional formulations well known in the art, for example as described in standard textbooks of pharmaceutics such as the British Pharmacopoeia.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

Clinically safe and effective dosages for the compounds with which the invention is concerned will be determined by clinical trials, as is required by the regulatory authorities in the art. It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

In the compounds used in the invention, examples of substituents R, to $R_4$ are given below:

The group $R_1$ $R_1$ may be, for example, hydrogen, methyl, ethyl, n-propyl, n-butyl, isobutyl, hydroxyl, methoxy, allyl, phenylpropyl, phenylprop-2-enyl, thienylsulphanylmethyl, thienylsulphinylmethyl, or thienylsulphonylmethyl; or $C_1$–$C_4$ alkyl,eg methyl, ethyl n-propyl or n-butyl, substituted by a phthalimido, 1,2-dimethyl-3,5-dioxo-1,2,4-triazolidin-4-yl, 3-methyl-2,5-dioxo-1-imidazolidinyl, 3,4,4-trimethyl-2,5-dioxo-1-imidazolidinyl, 2-methyl-3,5-dioxo-1,2,4-oxadiazol-4-yl, 3-methyl-2,4,5-trioxo-1-imidazolidinyl, 2,5-dioxo-3-phenyl-1-imidazolidinyl, 2-oxo-1-pyrrolidinyl, 2,5-ioxo-1-pyrrolidinyl or 2,6-dioxopiperidinyl, 5,5-dimethyl-2,4-dioxo-3-oxazolidinyl, hexahydro-1,3-dioxopyrazolo[1,2,a][1,2,4]-triazol-2-yl, or a naphththalimido (ie 1,3-dihydro-1,3-dioxo-2H-benz[f]isoindol-2-yl), 1,3-dihydro-1-oxo-2H-benz[f]isoindol-2-yl, 1,3-dihydro-1,3-dioxo-2H-pyrrolo[3,4-b]quinolin-2-yl, or 2,3-dihydro-1,3-dioxo-1H-benz[d,e]isoquinolin-2-yl group; or cyclohexyl, cyclooctyl, cycloheptyl, cyclopentyl, cyclobutyl, cyclopropyl, tetrahydropyranyl or morpholinyl.

Presently preferred $R_1$ groups include n-propyl, allyl, hydroxy, methoxy and thienylsulfanylmethyl.

The group $R_2$ $R_2$ may for example be $C_1$–$C_{12}$ alkyl, $C_3$–$C_6$ alkenyl or $C_3$–C6 alkynyl;

phenyl($C_1$–$C_6$ alkyl)-, phenyl($C_3$–$C_6$ alkenyl)- or phenyl($C_3$–$C_6$ alkynyl)- optionally substituted in the phenyl ring;

heteroaryl($C_1$–$C_6$ alkyl)-, heteroaryl($C_3$–$C_6$ alkenyl)- or heteroaryl($C_3$–$C_6$ alkynyl)- optionally substituted in the heteroaryl ring;

4-phenylphenyl($C_1$–$C_6$ alkyl)-, 4-phenylphenyl($C_3$–$C_6$ alkenyl)-, 4-phenylphenyl($C_3$–$C_6$ alkynyl)-, 4-heteroarylphenvl($C_1$–$C_6$ alkyl)-, 4-heteroarylphenyl($C_3$–$C_6$ alkenyl)-, 4-heteroarylphenyl($C_3$–$C_6$ alkynyl)-, optionally substituted in the terminal phenyl or heteroaryl ring;

phenoxy($C_1$–C6 alkyl)- or heteroaryloxy($C_1$–$C_6$ alkyl)- optionally substituted in the phenyl or heteroaryl ring;

Specific examples of such groups include methyl, ethyl, n- and iso-propyl, n-, iso- and tert-butyl, n-pentyl, n-hexyl, n-heptyl, n-nonyl, n-decyl, prop-2-yn-1-yl, 3-phenylprop-2-yn-1-yl, 3-(2-chlorophenyl)prop-2-yn-1-yl, phenylpropyl, 4-chlorophenylpropyl, 4-methylphenylpropyl, 4-methoxyphenylpropyl, phenoxybutyl, 3-(4-pyridylphenyl)propyl-, 3-(4-(4-pyridyl)phenyl)prop-2-yn-1-yl, 3-(4-phenylphenyl)propyl-, 3-(4-phenyl)phenyl)prop-2-yn-1-yl and 3-[(4-chlorophenyl)phenyl]propyl-, cyclopentylmethyl, and benzyl.

Presently preferred $R_2$ groups include isobutyl, n-hexyl, cyclopentylmethyl, benzyl, and 3-(2-chlorophenyl)prop-2-yn-1-yl.

The group $R_3$ $R_3$ may for example be $C_1$–$C_6$ alkyl, phenyl, 2,- 3-, or 4-hydroxyphenyl, 2,- 3-, or 4-methoxyphenyl, 2- or 3-thienyl, 2,- 3-, or 4-pyridylmethyl, benzyl, 2,- 3-, or 4-hydroxybenzyl, 2,- 3-, or 4-benzyloxybenzyl, 2,- 3-, or 4–$C_1$–$C_6$ alkoxybenzyl, or benzyloxy($C_1$–$C_6$alkyl)-group; or the characterising group of a natural α amino acid, in which any functional group may be protected, any amino group may be acylated and any carboxyl group present may be amidated; or a group -[Alk]$_n$$R_6$ where Alk is a ($C_1$–$C_6$)alkyl or ($C_2$–$C_6$)alkenyl group optionally interrupted by one or more —O—, or —S—atoms or —N($R_7$)— groups [where $R_7$ is a hydrogen atom or a ($C_1$–$C_6$)alkyl group], n is 0 or 1, and $R_6$ is an optionally substituted cycloalkyl or cycloalkenyl group; or a benzyl group substituted in the phenyl ring by a group of formula —OCH$_2$COR$_8$ where $R_8$ is hydroxyl, amino, ($C_1$–$C_6$)alkoxy, phenyl($C_1$–$C_6$)alkoxy, ($C_1$–$C_6$)alkylamino, di(($C_1$–$C_6$)alkyl)amino, phenyl ($C_1$–$C_6$)alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid; or a heterocyclic($C_1$–$C_6$)alkyl group, either being unsubstituted or mono- or di-substituted in the heterocyclic ring with halo, nitro, carboxy, ($C_1$–$C_6$)alkoxy, cyano, ($C_1$–$C_6$)alkanoyl, trifluoromethyl ($C_1$–$C_6$)alkyl, hydroxy, formyl, amino, ($C_1$–$C_6$)alkylamino, di-($C_1$–$C_6$)alkylamino, mercapto, ($C_1$–$C_6$)alkylthio, hydroxy($C_1$–$C_6$)alkyl, mercapto($C_1$–$C_6$)alkyl or ($C_1$–$C_6$)alkylphenylmethyl; or a group —CR$_a$R$_b$R$_c$ in which:

each of $R_a$, $R_b$ and $R_c$ is independently hydrogen, ($C_1$–$C_6$)alkyl, ($C_2$–$C_6$)alkenyl, ($C_2$–$C_6$)alkynyl, phenyl($C_1$–$C_6$)alkyl, ($C_3$–$C_8$)cycoalkyl; or $R_c$ is hydrogen and $R_a$and $R_b$ are independently phenyl or heteroaryl such as pyridyl; or $R_c$ is hydrogen, ($C_1$–$C_6$)alkyl, ($C_2$–$C_6$)alkenyl, ($C_2$–$C_6$)alkynyl, phenyl($C_1$–$C_6$)alkyl, or ($C_3$–$C_8$) cycloalkyl, and $R_a$ and $R_b$ together with the carbon atom to which they are attached form a 3 to 8 membered cycloalkyl or a 5- to 6-membered heterocyclic ring; or $R_a$, $R_b$ and $R_c$ together with the carbon atom to which they are attached form a tricyclic ring (for example adamantyl); or $R_a$ and $R_b$ are each independently ($C_1$–$C_6$)alkyl, ($C_2$–$C_6$)alkenyl, ($C_2$–$C_6$)alkynyl, phenyl($C_1$–$C_6$) alkyl, or a group as defined for $R_c$ below other than hydrogen, or $R_a$ and $R_b$ together with the carbon atom to which they are attached form a cycloalkyl or heterocyclic ring, and $R_c$ is hydrogen, —OH, —SH, halogen, —CN, —CO$_2$H, ($C_1$–$C_4$)perfluoroalkyl, —CH$_2$OH, —CO$_2$($C_1$–$C_6$)alkyl, —O($C_1$–$C_6$)alkyl, —O($C_2$–$C_6$)alkenyl, —S($C_1$–$C_6$)alkyl, —SO (C₁–C₆)alkyl, —SO₂(C₁–C₆) alkyl, —S(C₂–C₆) alkenyl, —SO(C₂–C₆)alkenyl, —SO₂(C₂–C₆) alkenyl or a group -Q-W wherein Q represents a bond or —O—, —S—, —SO— or —SO₂—and W represents a phenyl, phenylalkyl, (C₃–C₈) cycloalkyl, (C₃–C₈)cycloalkylalkyl, (C₄–C₈) cycloalkenyl, (C₄–C₈)cycloalkenylalkyl, heteroaryl or heteroarylalkyl group, which group W may optionally be substituted by one or more substituents independently selected from, hydroxyl, halogen, —CN, —CO₂H, —CO₂ (C₁–C₆)alkyl, —CONH₂, —CONH(C₁–C₆)alkyl, —CONH(C₁–C₆alkyl)₂, —CHO, —CH₂OH, (C₁–C₄)perfluoroalkyl, —O(C₁–C6)alkyl, —S(C₁–C₆)alkyl, —SO(C₁–C₆)alkyl, —SO₂ (C₁–C₆)alkyl, —NO₂, —NH₂, —NH(C₁–C₆) alkyl, —N((C₁–C₆)alkyl)₂, —NHCO(C₁–C₆) alkyl, (C₁–C₆)alkyl, (C₂–C₆)alkenyl, (C₂–C₆) alkynyl, (C₃–C₈)cycloalkyl, (C₄–C₈)cycloalkenyl, phenyl or benzyl.

Examples of particular R₃ groups include benzyl, phenyl, cyclohexylmethyl, pyridin-3-ylmethyl, tert-butoxymethyl, iso-butyl, sec-butyl, tert-butyl, 1-benzylthio-1-methylethyl, 1-methylthio-1-methylethyl, and 1-mercapto-1-methylethyl.

Presently preferred R₃ groups include phenyl, benzyl, tert-butoxymethyl and iso-butyl.

The group R₄

Examples of particular ester and thioester groups R₄ groups include those of formula —(C=O)OR₉, —(C=O) SR₉, —(C=S)SR₉, and —(C=S)OR₉ wherein R₉ is (C₁–C₆)alkyl, (C₂–C₆)alkenyl, cycloalkyl, cycloalkyl (C₁–C₆)alkyl-, phenyl, heterocyclyl, phenyl(C₁–C₆)alkyl-, heterocyclyl(C₁–C₆)alkyl-, (C₁–C₆)alkoxy(C₁–C₆)alkyl-, (C₁–C₆)alkoxy(C₁–C₆)alkoxy(C₁–C₆)alkyl-, any of which may be substituted on a ring or non-ring carbon atom or on a ring heteroatom, if present. Examples of such R₉ groups include methyl, ethyl, n-and iso-propyl, n-, sec- and tert-butyl, 1-ethyl-prop-1-yl, 1-methyl-prop-1-yl, 1-methyl-but-1-yl, cyclopentyl, cyclohexyl, allyl, phenyl, benzyl, 2-, 3- and 4-pyridylmethyl, N-methylpiperidin4-yl, 1-methylcyclopent-1yl, adamantyl, tetrahydrofuran-3-yl and methoxyethyl.

Presently preferred are compounds of formula (I) wherein R₄ is a carboxylate ester of formula —(C=O)OR₉, wherein R₉ is benzyl, cyclopentyl, isopropyl or tert-butyl.

The group R

Presently preferred R groups are hydrogen and methyl.

Compounds used according to the present invention may be prepared by the methods described in our published international patent application No WO 98/11063. Specific examples of compounds which may be used are those of the following examples 1–50. Examples 1–42 are compounds disclosed in WO 98/11063.

A compound presently preferred for its potency as an intracellular LTA4 inhibitor is that of Example 19, namely 2S-(3S-hydroxycarbamoyl-2R-isobutyl-hex-5-enoylamino)-3-phenylpropionic acid cyclopentyl ester, and pharmaceutically acceptable salts, hydrates and esters thereof.

EXAMPLE 1

(Example 1 of WO 98/11063)

2S-(3S-Hydroxycarbamoyl-2R-isobutyl-hex-5-enoylamino)-3-phenylpropionic acid methyl ester.

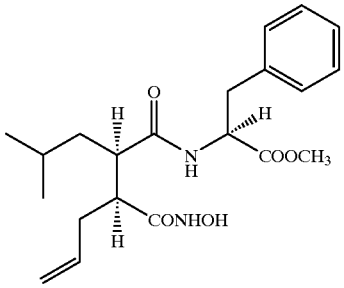

EXAMPLE 2

(Example 2 of WO 98/11063)

2S-(3S-Hydroxycarbamoyl-2R-isobutyl-hex-5-enoylamino)-3-phenylpropionic acid ethyl ester.

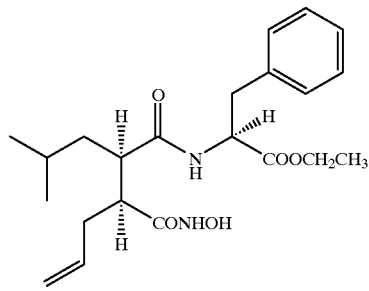

EXAMPLE 3

(Example 3 of WO 98/11063)

2S-(3S-Hydroxycarbamoyl-2R-isobutyl-hex-5-enoylamino)-3-phenylpropionic acid isopropyl ester.

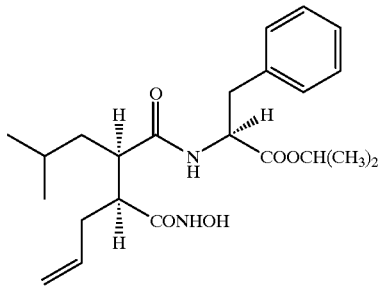

EXAMPLE 4

(Example 5 of WO 98/11063)

3R-(2-Phenyl-1S-methylcarboxy-ethylcarbamoyl)-2S,5-imethylhexanohydroxamic acid

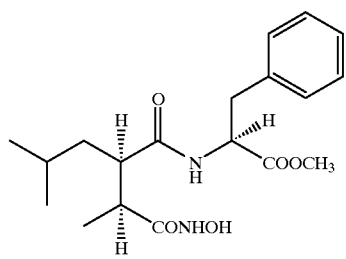

EXAMPLE 5

(Example 6 of WO 98/11063)

2S-(3S-Hydroxycarbamoyl-2R-isobutyl-hex-5-enoylamino)-3-phenyl-propionic acid tert-butyl ester

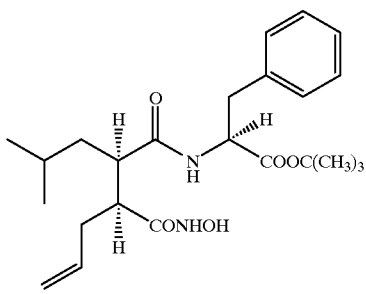

EXAMPLE 6

(Example 7 of WO 98/11063)

2S-(2R-Hydroxycarbamoylmethyl-4-methyl-pentanoylamino)-3-phenyl-propionic acid isopropyl ester

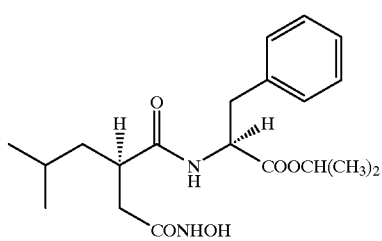

EXAMPLE 7

(Example 8 of WO 98/11063)

2S-[2R-(S-Hydroxy-hydroxycarbamoyl-methyl)-4-methyl-pentanoylamine]-3-phenyl-propionic acid isopropyl ester.

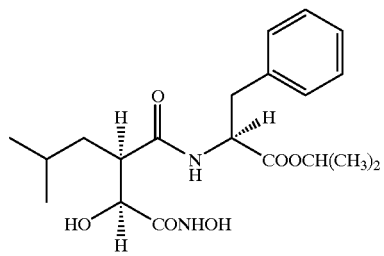

EXAMPLE 8

(Example 9 of WO 98/11063)

2S-[2R-(1S-Hydroxycarbamoylethyl)-4-methyl-pentanoylamino]-3-phenyl-propionic acid isopropyl ester.

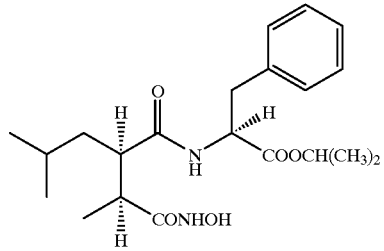

EXAMPLE 9

(Example 10 of WO 98/11063)

2S-(2R-Hydroxycarbamoylmethyl-octanoylamino)-3-phenyl-propionic acid isopropyl ester.

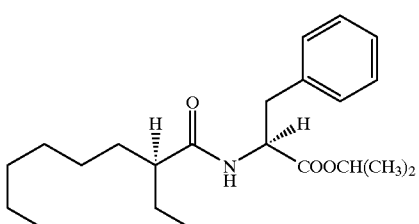

EXAMPLE 10

(Example 11 of WO 98/11063)

2S-[2R-(S-Hydroxy-hydroxycarbamoyl-methyl)-4-methyl-pentanoylamino]-3-phenyl-propionic acid cyclopentyl ester.

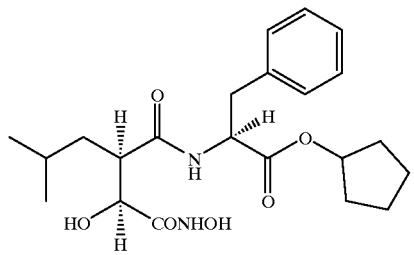

EXAMPLE 11

(Example 12 of WO 98/11063)

2 S-(3S-Hydroxycarbamoyl-2R-isobutyl-hex-5-enoylamino)-3S-methy-pentanoic acid cyclopentyl ester.

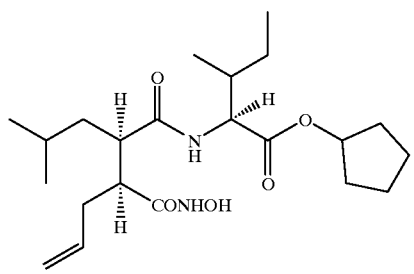

EXAMPLE 12

(Example 13 of WO 98/11063)

2S-(3S-Hydroxycarbamoyl-2R-isobutyl-hex-5-enoylamino)-3-phenylpropionic acid 2-methoxy-ethyl ester.

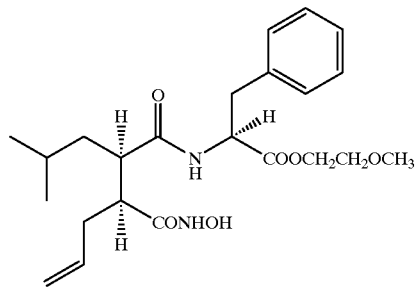

EXAMPLE 13

(Example 1 of WO 98/11063)

2S-[2R-(1S-Hydroxycarbamoyl-ethyl)-4-methyl-pentanoylamino]-3-phenyl-propionic acid 2-methoxy-ethyl ester.

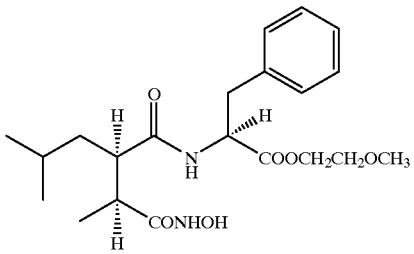

EXAMPLE 14

(Example 15 of WO 98/11063)

2S-(3S-Hydroxycarbamoyl-2R-isobutyl-hexanoylamino)-3,3-dimethyl-butyric acid 2-methoxy-ethyl ester.

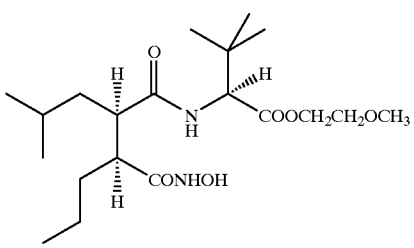

EXAMPLE 15

(Example 1 of WO 98/11063)

2S-[2R-(S-Hydroxycarbamoyl-methoxy-methyl)-4-methyl-pentanoylamino]-3-phenyl-propionic acid isopropyl ester.

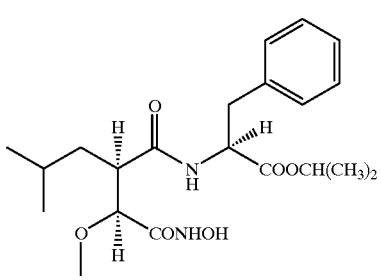

EXAMPLE 16

(Example 17 of WO 98/11063)

2S-{2R-[1S-Hydroxycarbamoyl-2-(thiophen-2-ylsulphanyl)-ethyl]-4-methyl-pentanoylamino}-3-phenyl-propionic acid isopropyl ester.

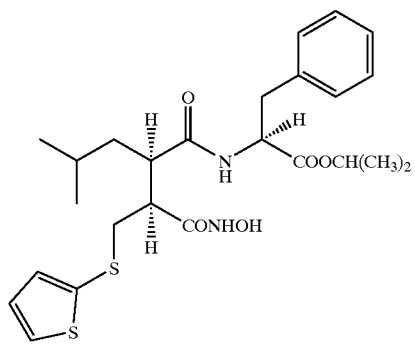

EXAMPLE 17

(Example 18 of WO 98/11063)

2S-[2-R-(1S-Hydroxycarbamoyl-ethyl)-4-methyl-pentanoylamino]-3,3-dimethyl-butyric acid 2-methoxy-ethyl ester.

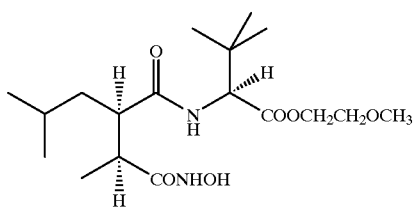

EXAMPLE 18

(Example 19 of WO 98/11063)

2S-(3S-Hydroxycarbamoyl-2R-isobutyl-hex-5-enoylamino)-3,3-dimethyl-butyric acid 2-methoxy-ethyl ester.

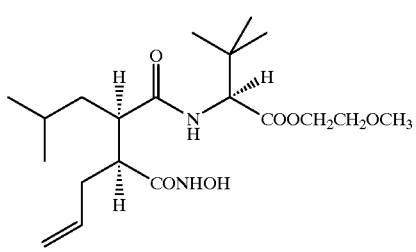

EXAMPLE 19

(Example 20 of WO 98/11063)

2S-(3S-Hydroxycarbamoyl-2R-isobutyl-hex-5-enoylamin)-3-phenylpropionic acid cyclopentyl ester.

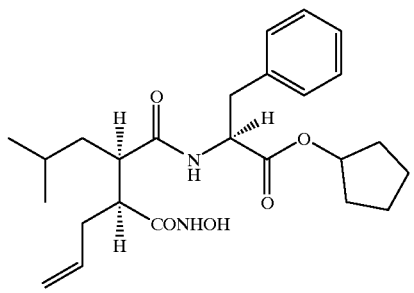

EXAMPLE 20

(Example 21 of WO 98/11063)

2S-(3S-Hydroxycarbamoyl-2R-isobutyl-hexanoylamino)-3-phenylpropionic acid isopropyl ester.

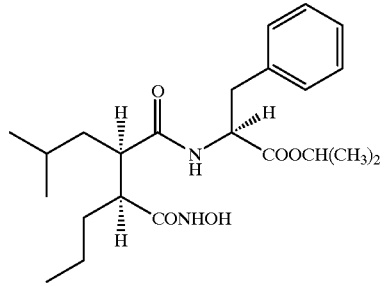

EXAMPLE 21

(Example 22 of WO 98/11063)

2S-(3S-Hydroxycarbamoyl-2R-isobutyl-hex-5-enoylamino)-3,3-dimethyl-butyric acid isopropyl ester.

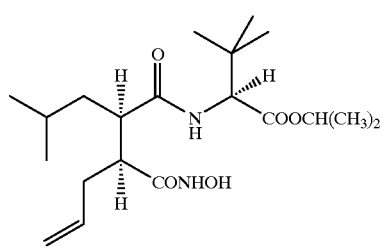

EXAMPLE 22

(Example 23 of WO 98/11063)

2R-(3S-Hydroxycarbamoyl-2R-isobutyl-hex-5-enoylamino)-3-phenylpropionic acid isopropyl ester.

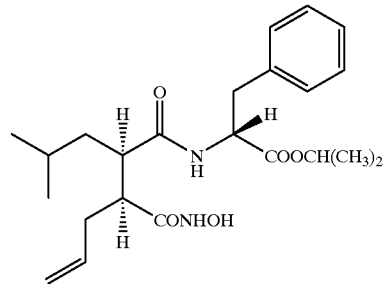

EXAMPLE 23

(Example 24 of WO 98/11063)

2S-[2R-(S-Hydroxycarbamoyl-methoxy-methyl )-4-methyl-pentanoylamino]-3,3-dimethyl-butyric acid isopropyl ester.

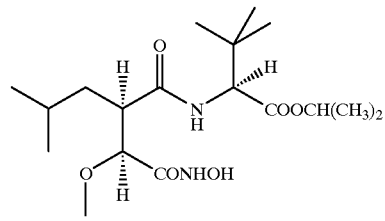

EXAMPLE 24

(Example 25 of WO 98/11063)

2S-{(3S-Hydroxycarbamoyl-2R-isobutyl-hex-5-enoyl)-methyl-amino}-3-phenylpropionic acid isopropyl ester.

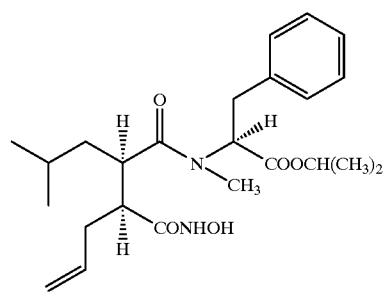

EXAMPLE 25

(Example 26 of WO 98/11063)

2S-(3S-Hydroxycarbamoyl-2R-isobutyl-hex-5-enoylamino)-3-phenylpropionic acid benzyl ester.

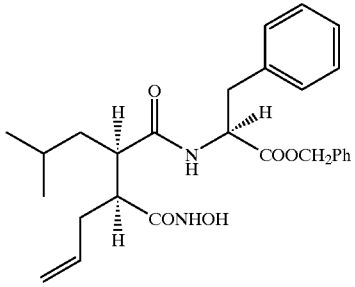

EXAMPLE 26

(Example 27 of WO 98/11063)

2S-(3S-Hydroxycarbamoyl-2R-isobutyl-hex-5-enoylamino)-4-methyl-pentanoic acid cyclopentyl ester.

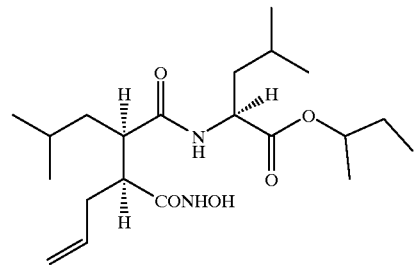

EXAMPLE 27

(Example 28 of WO 98/11063)

3-Cyclohexyl-2S-(3S-hydroxycarbamoyl-2R-isobutyl-hex-5-enoylamino)-propionic acid cyclopentyl ester.

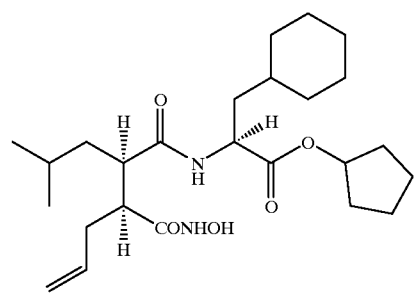

EXAMPLE 28

(Example 29 of WO 98/11063)

2S-(3S-Hydroxycarbamoyl-2R-isobutyl-hex-5-enoylamino)-3-phenylpropionic acid 1-methyl-piperidin-4-yl ester.

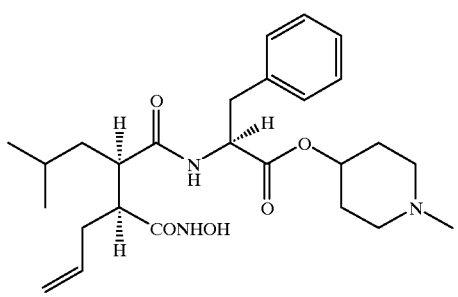

EXAMPLE 29

(Example 30 of WO 98/11063)

2S-(3S-Hydroxycarbamoyl-2R-isobutyl-hex-5-enoylamino)-3-phenylpropionic acid 1-ethyl-propyl ester.

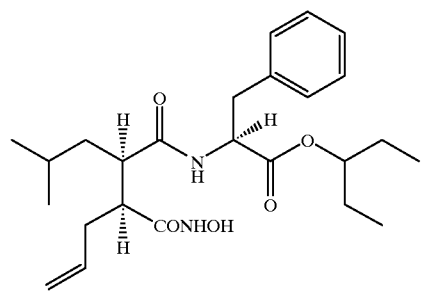

EXAMPLE 30

(Example 31 of WO 98/11063)

2S-(3S-Hydroxycarbamoyl-2R-isobutyl-hex-5-enoylamino)-3-phenylpropionic acid 1S-methyl-butyl ester.

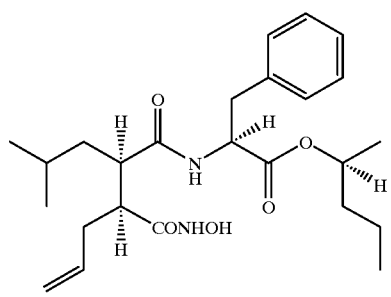

EXAMPLE 31

(Example 32 of WO 98/11063)

2S-(3S-Hydroxycarbamoyl-2R-isobutyl-hex-5-enoylamino)-3-phenylpropionic acid cyclohexyl ester.

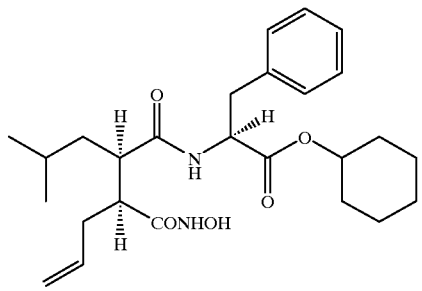

EXAMPLE 32

(Example 1 of WO 98/11063)

2S2R-[1S-Hydroxycarbamoyl-2-(thiophen-2-ylsulphanyl)-ethyl]-4-methyl-pentanoylamino}-3,3-imethyl-butyric acid isopropyl ester.

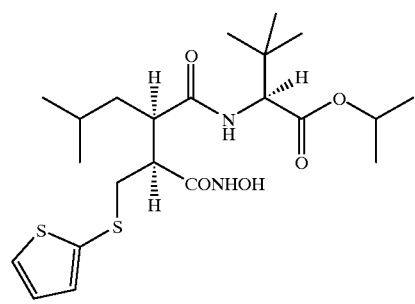

EXAMPLE 33

(Example 34 of WO 98/11063)

2S(3-Hydroxycarbamoyl-2R-isobutyl-hex-5-enoylamino)-3-phenylpropionic acid 1R-methyl-butyl ester.

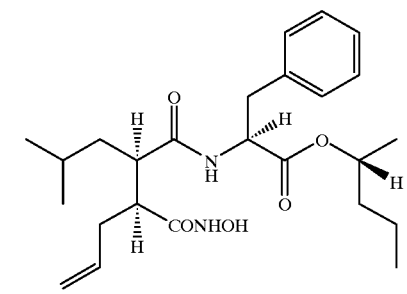

EXAMPLE 34

(Example 35 of WO 98/11063)

2S-(3S-Hydroxycarbamoyl-2R-isobutyl-hex-5-enoylamino)-3-phenylpropionic acid tetrahydro-furan-3(R,S)-yl ester.

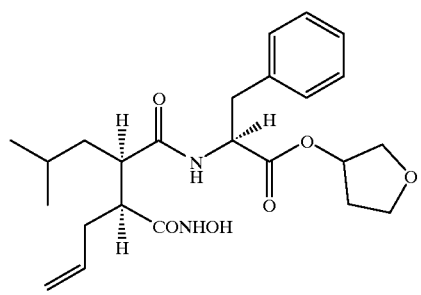

EXAMPLE 35

(Example 36 of WO 98/11063)

2S-(3S-Hydroxycarbamoyl-2R-isobutyl-hex-5-enoylamino)-3,3-dimethyl-butyric acid cyclopentyl ester.

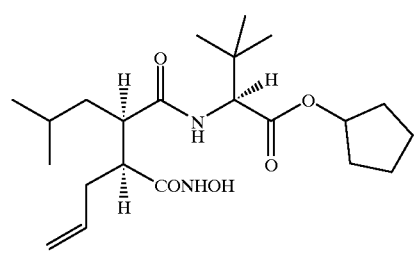

EXAMPLE 36

(Example 37 of WO 98/11063)

2S-[2R-(1S-Cyclopentyl-hydroxycarbamoyl-methyl)-4-methyl-pentanoylamino]-3-phenyl-propionic acid cyclopentyl ester.

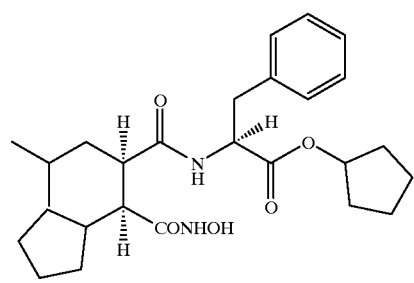

EXAMPLE 37

(Example 38 of WO 98/11063)

2S-[2R-(1S-Hydroxy-hydroxycarbamoyl-methyl)-pent-4-ynoylamino]-3-phenylpropionic acid cyclopentyl ester.

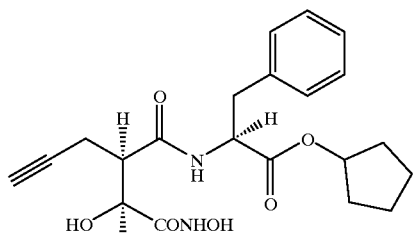

EXAMPLE 38

(Example 39 of WO 98/11063)

2S-(3S-Hydroxycartamoyl-2R-isobutyl-hex-5-enoylamino)-3-pyridin-3-yl-propionic acid cyclopentyl ester.

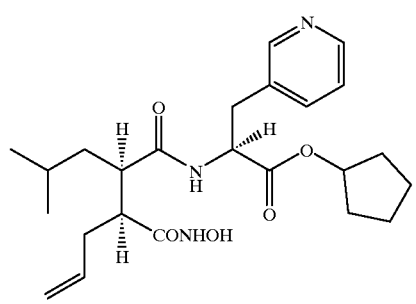

EXAMPLE 39

(Example 40 of WO 98/11063)

3-tert-Butoxy-2S-(3S-hydroxycarbamoyl-2R-isobutyl-hex-5-enoylamino)-propionic acid cyclopentyl ester.

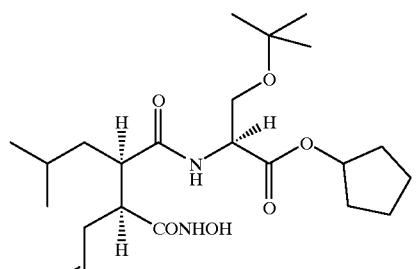

EXAMPLE 40

(Example 41 of WO 98/11063)

2S-(3S-Hydroxycarbamoyl-2R-isobutyl-hex-5-enoylamino)-2-phenylethanoic acid cyclopentyl ester.

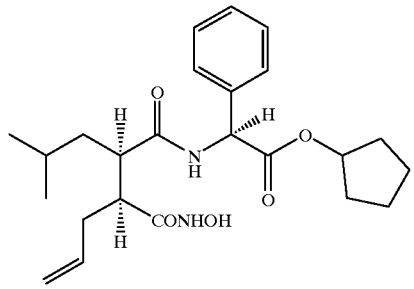

EXAMPLE 41

(Example 42 of WO 98/11063)

2S-[5-(2-Chlorophenyl)-2R-(1S-hydroxy-hydroxycarbamoyl-methyl)-pent-4-ynoylamino]-3-phenylpropionic acid cyclopentyl ester.

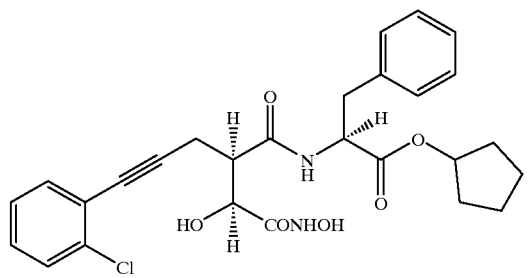

EXAMPLE 42

(Example 43 of WO 98/11063)

2S-(3S-Hydroxycarbamoyl-2R-isobutyl-6-phenyl-hex-5-enoylamino)-3-phenyl-propionic acid cyclopentyl ester.

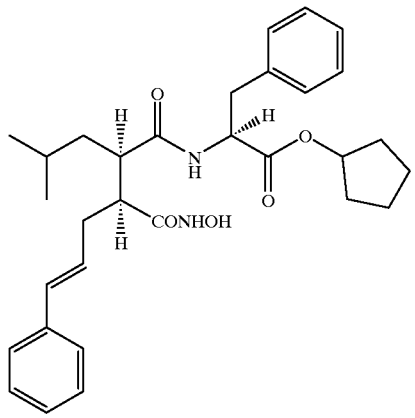

EXAMPLE 43

2-[2R-(S-Hydroxy-hydroxycarbamoyl-methyl)-4-methyl-pentanoylamine]-2-phenyl-ethanoic acid cyclopentyl ester.

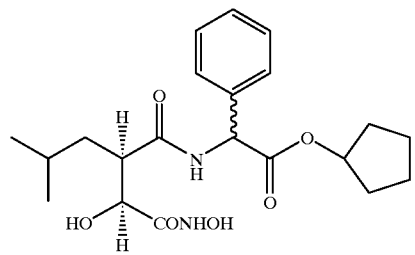

Prepared using procedures similar to those described in example 8 of WO 98/11063, using phenylglycine cyclopentyl ester.

Diastereoisomer A $^1$H-NMR; δ (MeOD), 7.4–7.29 (5H, m), 5.43 (1H, s), 5.2–5.14 (1H, m), 4.02 (1H, d, J=6.9Hz), 2.94–2.85 (1H, m), 1.91–1.34 (10H, bm), 1.25–1.14 (1H, m) and 0.86, dd, J=6.5, 11.5Hz). $^{13}$C-NMR; δ (MeOD), 175.6, 171.8, 171.4, 137.8, 129.8, 129.4, 128.6, 80.0, 73.2, 58.5, 49.2, 39.1, 33.3, 33.3, 26.8, 24.5, 24.4, 23.7 and 22.1.

Diastereoisomer B $^1$H-NMR; δ (MeOD), 7.33–7.19 (5H, m), 5.3 (1H, s), 5.11–5.06 (1H, m), 3.81 (1H, d, J=7.3Hz), 2.83–2.74 (1H, m), 1.83–1.45 (10H, bm), 1.12–1.03 (1H, m) and 0.88–0.81 (6H, dd, J=6.4, 12.3Hz). $^{13}$C-NMR; δ (MeOD), 175.8, 171.8, 171.5, 137.3, 129.8, 129.5, 128.8, 79.9, 73.3, 58.7, 48.9, 39.2, 33.3, 33.3, 26.7, 24.5, 24.5, 24.0 and 22.2.

EXAMPLE 44

2-(3S-Hydroxycarbamoyl-2R-isobutyl-hex-5-enoylamino)-2-phenylethanoic acid isopropyl ester

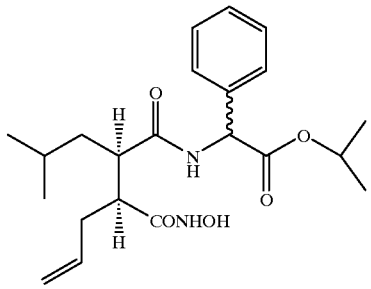

Prepared using methods similar to those described in example 41 of application WO 98/11063 using phenylglycine isopropyl ester.

Diastereoisomer A $^1$H-NMR; δ (MeOD), 7.34–7.24 (5H, m), 5.59–5.42 (1H, m), 5.36 (1H, s), 5.02–4.77 (3H, m), 2.63–2.53 (1H, m), 2.17–2.02 (2H, m), 1.89–1.78 (1H, m), 1.63–1.4 (2H, m), 1.18 (3H, d, J=6.3Hz), 1.05 (3H, d, J=6.2Hz), 1.00–0.93 (1H, m), 0.88 (3H, d, J=6.5Hz) and 0.81 (3H, d, J=6.5Hz). $^{13}$C-NMR; δ (MeOD), 176.2, 172.4, 171.3, 137.6, 136.0, 129.9, 129.6, 129.0, 117.4, 70.5, 58.7, 47.4, 41.5, 36.0, 26.7, 24.5, 21.9, 21.7 and 21.7.

Diastereoisomer B $^1$H-NMR; δ (MeOD), 7.4–7.34 (5H, m), 5.77–5.61 (1H, m), 5.42 (1H, s), 5.1–4.98 (3H, m), 2.7–2.6 (1H, m), 2.44–2.17 (3H, m), 1.61–1.5 (1H, m), 1.42–1.29 (1H, m), 1.25 (3H, d, J=6.3Hz), 1.13 (3H, d, J=6.2Hz), 1.09–1.00 (1H, m) and 0.81 (6H, d, J=6.4Hz). $^{13}$C-NMR; δ (MeOD), 176.4, 172.5, 171.5, 137.2, 136.4, 129.9, 129.6, 129.0, 117.5, 70.5, 58.8, 48.4, 47.4, 41.3, 36.0, 27.1, 24.3, 21.9, 21.8 and 21.6.

EXAMPLE 45

2-[2R-(S-Hydroxycarbamoyl-methoxy-methyl)-4-methyl-pentanoylamino]-3-phenylethanoic acid cyclopentyl ester

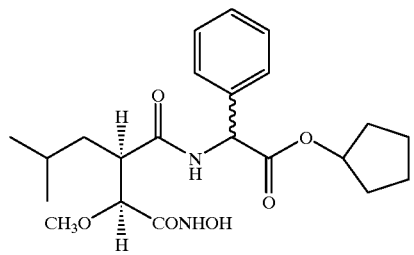

Prepared using methods similar to those described in example 16 of application WO 98/11063, using phenylglycine cyclopentyl ester.

Diastereoisomer A $^1$H-NMR; δ (MeOD), 8.83 (1H, d, J=6.6Hz), 7.48–7.29 (5H, m), 5.44–5.42 (1H, m), 5.20–5.16 (1H, m), 3.53 (1H, d, J=9.7Hz), 3.17 (3H, s), 2.89–2.79 (1H, m), 1.90–1.54 (10H, bm), 1.06–0.99 (1H, m), 0.95 (3H, d, J=6.5Hz) and 0.90 (3H, d, J=6.4Hz). $^{13}$C-NMR; δ (MeOD), 175.3, 171.6, 169.4, 137.5, 129.7, 129.4, 128.7, 83.1, 79.9, 58.7, 58.1, 48.5, 38.4, 33.4, 33.3, 26.7, 24.6, 24.5, 24.3 and 21.8.

Diastereoisomer B $^1$H-NMR; δ (MeOD), 7.39–7.30 (5H, m), 5.45 (1H, s), 5.21–5.15 (1H, m), 3.59 (1H, d, J=9.4Hz), 3.29 (3H, s), 2.89–2.79 (1H, m), 1.93–1.49 (9H, bm), 1.42–1.21 (1H, m), 1.01 (1H, ddd, J=3.7, 9.9, 13.3Hz), 0.83 (3H, d, J=6.5Hz) and 0.79 (3H, d, J=6.6HHz). $^{13}$C-NMR; δ (MeOD), 175.1, 171.5, 169.5, 137.9, 129.7, 129.4, 128.7, 83.0, 79.8, 58.5, 58.3, 48.6, 38.5, 33.3, 27.8, 24.5, 24.4, 24.1 and 21.7.

EXAMPLE 46

2-(3S-Hydroxycarbamoyl-2R-isobutyl-hex-5-enoylamino)-2-(4-methoxyphenyl)ethanoic acid cyclopentyl ester

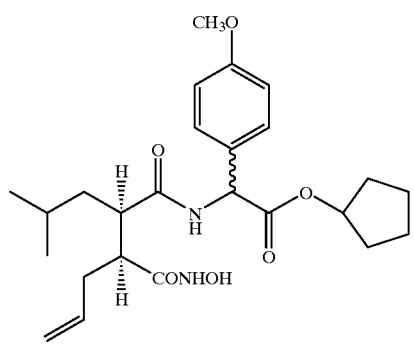

Prepared using methods similar to those described in exampie 41 of application WO 98/11063, using 4-methoxyphenylglycine cyclopentyl ester.

Diastereoisomer A $^1$H-NMR; δ (MeOD), 8.94 (1H, d, J=6.4Hz), 7.32 (2H, d, J=8.7Hz), 6.93 (2H, d, J=8.7Hz), 5.67–5.50 (1H, m), 5.36–5.33 (1H, m), 5.20–5.14 (1H, m). 4.93–4.87 (2H m), 3.79 (3H, s), 2.68–2.59 (1H, m), 2.24–2.09 (2H, m), 1.97–1.55 (11H, bm), 1.11–1.00 (1H, m), 0.95 (3H, d, J=6.5Hz) and 0.88 (3H, d, J=6.5Hz). $^{13}$C-NMR; δ (MeOD), 176.2, 172.4, 171.9, 161.4, 136.0, 130.2, 129.4, 117.4, 115.2, 79.7, 58.2, 55.8, 48.3. 47.3, 41.5, 36.0, 33.4, 33.3, 26.7, 24.6, 24.5 and 21.7.

Diastereoisomer B $^1$H-NMR; δ (MeOD), 8.96 (1H, d, J=6.7Hz), 7.29 (2H, d, J=8.7Hz), 6.93 (2H, d, J=8.7Hz), 5.77–5.61 (1H, m), 5.32 (1H, s), 5.20–5.15 (1H, m), 5.09–4.97 (2H, m), 3.80 (3H, s), 2.64 (1 H, dt. J=3.3, 11.4, 13.5Hz), 2.43–2.16 (3H, m), 1.91–1.49 (9H, bm), 1.42–1.29 (1H, m), 1.05 (1H, ddd, J=3.3, 10.1, 13.2Hz) and 0.81 (6H, d, J=6.5Hz). $^{13}$C-NMR; δ (MeOD), 176.3, 172.5, 172.0, 161.4, 136.4, 130.2, 129.0, 117.5, 115.2, 79.8, 58.2, 55.8, 48.4, 47.4, 41.3, 36.1, 33.4, 27.1, 24.5, 24.3 and 21.6.

EXAMPLE 47

2-(3S-Hydroxycarbamoyl-2R-isobutyl-hex-5-enoylamino)-2-(thien-2-yl)ethanoic acid cyclopentyl ester

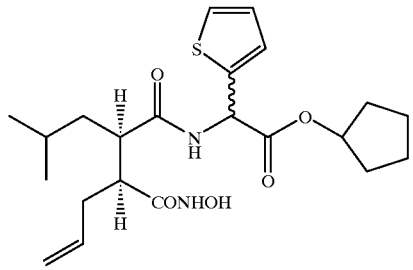

Prepared using methods similar to those described in example 41 of application WO 98/11063, using thien-2-ylglycine cyclopentyl ester.

Diastereoisomer A $^1$H-NMR; δ (MeOD), 7.41 (1H, dd, J=5.1. 1.2Hz), 7.12 (1H, d, J=3.5Hz), 7.01 (1H, dd, J=5.1, 3.5Hz), 5.72 (1H, s), 5.69–5.52 (1H, m), 5.26–5.18 (1H, m), 5.004.89 (2H, m), 2.70–2.59 (1H, m), 2.28–2.13 (2H, m), 2.09–1.50 (11H, m), 1.05 (1H, ddd, J=13.8. 11.0, 2.9Hz), 0.93 (3H, d, J=6.4Hz) and 0.87 (3H, d, J=6.5Hz). $^{13}$C-NMR; δ (MeOD), 176.5, 172.7, 171.1, 139.5, 136.4, 128.4, 128.3, 127.7, 117.9, 80.7, 54.1, 48.7, 47.7, 41.9, 36.5, 33.8, 33.7, 27.2, 25.1, 25.0, 24.9, and 22.1.

Diastereoisomer B $^1$H-NMR; δ (MeOD), 7.42 (1H, dd, J=5.0, 0.7Hz), 7.10 (1H, d, J=3.6Hz), 7.01 (1H, dd, J=5.0, 3.6Hz), 5.79–5.59 (2H, m), 5.28–5.19 (1H, m), 5.104.94 (2H, m), 2.71–2.59 (1H, m), 2.36–2.16 (3H, m), 1.97–1.34 (10H, m), 1.13–1.00 (1H, m), 0.86 (3H, d, J=6.2Hz) and 0.84 (3H, d, J=6.3Hz). $^{13}$C-NMR; δ (MeOD), 176.7, 172.8, 171.2, 139.3, 136.7, 128.3, 128.2, 127.6, 117.9, 80.7, 54.2, 48.8, 47.8, 41.7, 36.4, 33.8, 27.5, 25.1, 25.0, 24.8 and 22.1.

EXAMPLE 48

2-(3S-Hydroxycarbamoyl-2R-isobutyl-hex-5-enoylamino)-2-(thien-3-yl)ethanoic acid cyclopentyl ester

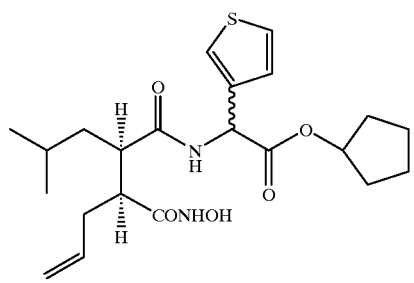

Prepared using methods similar to those described in example 41 of application WO 98/11063, using thien-3-ylglycine cyclopentyl ester.

Diastereoisomer A

¹H-NMR; δ (MeOD), 7.48–7.42 (2H, m), 7.13 (1H, dd, J=4.2, 2.0Hz), 5.69–5.52 (2H, m), 5.21–5.16 (1H, m), 4.98–4.90 (2H, m), 2.71–2.59 (1H, m), 2.28–2.11 (2H, m), 2.00–1.50 (11H, m), 1.12–0.98 (1H, m), 0.94 (3H, d, J=6.4Hz) and 0.88 (3H, d, J=6.5Hz). ¹³C-NMR; δ (MeOD), 176.6, 172.8, 171.8, 137.8, 136.4, 128.3, 128.0, 125.2, 117.9, 80.3, 54.6, 41.9, 36.5, 33.8, 33.8, 27.1, 25.0, 24.9 and 22.1.

Diastereoisomer B

¹H-NMR; δ (MeOD), 7.45 (1H, dd, J=4.9, 3.0Hz), 7.43–7.40 (1H, m), 7.12 (1H, dd, J=5.0, 1.3Hz), 5.68 (1H, ddt, J=17.0, 10.1, 6.8Hz), 5.53 (1H, s), 5.23–5.17 (1H, m), 5.10–4.96 (2H, m), 2.70–2.60 (1H, m), 2.41–2.16 (3H, m), 1.94–1.49 (9H, m), 1.44–1.29 (1H, m), 1.05 (1H, ddd, J=12.9, 10.3, 3.3Hz), 0.84 (3H, d, J=6.5Hz) and 0.83 (3H, d, J=6.5Hz).

EXAMPLE 49

2S-[2R-(S-Hydroxy-hydroxycarbamoyl-methyl)-3-phenyl-propanoylamine]-2-phenyl-ethanoic acid cyclopentyl ester.

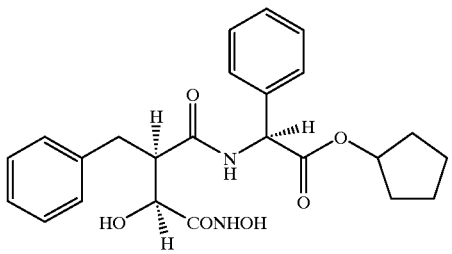

This compound was prepared using the method of example 11 of patent application WO 98/11063 and intermediates similar to those described in patent application WO 95/19956. ¹H-NMR; δ (MeOD), 7.39–7.15 (10H, m), 5.32 (1H, s), 5,15–5.06 (1H, m), 4.05 (1H, d, J=5.7Hz), 3.19–3.10 (1H, m), 3.02–2.81 (2H, m) and 1.89–1.40 (8H, m). ¹³C-NMR; δ (MeOD), 175.4, 172.1, 171.8, 140.2, 137.9. 130.6, 130.1, 129.9, 129.7, 128.9, 80.4, 72.7, 58.6, 52.4, 36.5, 33.7, 24.9 and 24.8.

EXAMPLE 50

2S-(3S-Hydroxycarbamoyl-2R-cyclopentylmethyl-hex-5-enoylamino)-2-phenyl-ethanoic acid cyclopentyl ester.

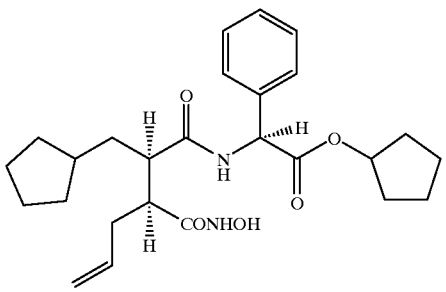

This ccmpound was prepared using the method described for example 1 of patent application WO 98/11063 and intermediates similar to those described in patent application WO 94/21625. ¹H-NMR; δ (MeOD), 9.02 (1H, m), 7.40 (5H, m), 5.60 (1H, m), 5.45 (1H, m), 5,17 (1H, m), 4.90 (2H, m), 2.61 (1H, m), 2.20 (2H, m), 2.05–1.40 (17H, m) and 1.10 (3H, m).

Biological Example A

LTA₄-hydoiase was prepared as a crude fraction from rat lung tissue. The sodium salt of LTA₄ was incubated with the enzyme and test compounds at 10 μM for 1 minute at 37° C. The reaction was terminated by the addition of ice-cold methanol. Formation of LTB₄ was assessed by radioimmunoassay. Results are expressed as a percentage inhibition of LTA₄ hydrolase activity.

The results obtained are expressed in the following table

| Compound | % Inhibition at 10 μM |
|---|---|
| Example 40 | 75 |
| Example 19 | 78 |

For comparison the known LTA₄-hydrolase inhibitor kelatorphan inhibits activity by 80% at 10 μM.

Biological Example B

Inhibition of Leukotriene Synthesis by Rat Basophilic Leukaemia Cells

The rat basophilic leukaemia cell line RBL-1 was obtained from ATCC or ECACC and cultured in Dulbecco's modified Eagle's medium (DMEM) supplemented with 10% foetal bovine serum, non-essential amino acids, sodium pyruvate, penicillin, streptomycin and 2mM glutamine, at 37° C. in an atmosphere of 5% CO₂ in air, as recommended by the culture collection.

RBL-1 cells were harvested during log growth, washed and resuspended in Hanks Balanced Salt Solution, without calcium chloride and magnesium chloride, supplemented with 10% foetal bovine serum and penicillin, streptomycin, and 2mM glutamine and adjusted to a final cell concentration of 1.25×10⁵ cells/ml. Cells incubated in the presence of the appropriate concentration of inhibitor or vehicle for 4.75 hours at 37° C. Cells then transferred to ice for 15 minutes. Cells washed by centrifugation and resuspension in pre-chilled Phosphate Buffered Saline, with calcium chloride and magnesium chloride, supplemented with the appropriate concentration of test sample. After the PBS wash, cells resuspended at a final cell concentration of equivalent to 2.35×10⁶ cell/ml in PBS/sample buffer. Cells transferred to a microfuge tube on ice prior to ionophore stimulation.

Treated cells then exposed to 10 μM A23187 for 15 minutes at 37° C. Cells transferred to ice, thereby stopping the reaction. Cell free supernatant harvested by centrifugation. The levels of leukotriene $B_4$ then determined in the cell free supernatant using the Leukotriene $B_4$[³H] assay system from Amersham Pharmacia Biotech.

Using this methodology the $IC_{50}$ value for the compound of example 19 was estimated as 2nM and for Kelatorphan as 350nM.

Biological Example C

Rat Adjuvant Arthritis Model

Adjuvant arthritis was induced in male Lewis rats on Day 0, using a suspension of *mycobacterium butyncum* in mineral oil, inoculated subcutaneously, into the base of the tail. The volume of the hind paws was measured regularly to assess the time course of disease progression. On Day 10 animals were randomised into treatment groups, to ensure that each group had a similar mean hind paw volume at the start of treatment. Nine animals were allocated to each group. Animals received their first treatment on Day 10, either vehicle (2% DMSO in PBSiTween (0.01%v/v)) or test compound, formulated as a suspension in the vehicle. Treatment was administered as an intraperitoneal bolus injection, once daily, for the duration of the study. The study was ended on Day 21. The percent increase in mean paw volume from Day 10 to Day 21 was calculated for each animal and the compound treated groups compared to the vehicle treated control group.

The compound of example 19, administered at 30mg/kg and 100mg/kg i.p., inhibited paw swelling by 60% and 77% respectively. This inhibition was statistically significant (P<0.05) at both doses.

What is claimed is:

1. A method of treatment of mammals suffering diseases responsive to inhibition of intracellular leukotriene-$A_4$ hydrolase activity, comprising administering to the mammal suffering such disease an amount of a compound of formula (I) or a pharmaceutically accepted salt hydrate or solvate thereof to inhibit such activity

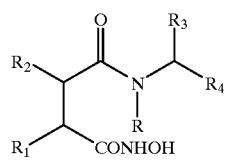

(I)

wherein

R is hydrogen or ($C_1$–$C_6$)alkyl;

$R_1$ is hydrogen;
 ($C_1$–$C_6$)allkyl;
 ($C_2$–$C_6$)alkenyl;
 phenyl or substituted phenyl;
 phenyl ($C_1$–$C_6$)alkyl or substituted phenyl($C_1$–$C_6$) alkyl;
 phenyl ($C_2$–$C_6$)alkenyl or substituted phenyl($C_2$–$C_6$) alkenyl
 heterocyclyl or substituted heterocyclyl;
 heterocyclyl($C_1$–$C_8$)alkyl or substituted heterocyclyl ($C_1$–$C_6$)alkyl;
 a group $BSO_nA$- wherein n is 0, 1 or 2 and B is hydrogen or a ($C_1$–$C_6$)alkyl,
 phenyl, substituted phenyl, heterocyclyl substituted heterocyclyl, ($C_1$–$C_6$)acyl, phenacyl or substituted phenacyl group, and A represents ($C_1$–$C_6$)alkylene;
 hydroxy or ($C_1$–$C_6$)alkoxy;
 amino, protected amino, acylamino, ($C_1$–$C_6$) alkylamino or di-($C_1$–$C_6$)alkylamino;
 mercapto or ($C_1$–$C_6$)alkylthio;
 amino($C_1$–$C_6$)alkyl, ($C_1$–$C_6$)alkylamino($C_1$–$C_6$)alkyl, di-($C_1$–$C_6$) alkylamino($C_1$–$C_6$)alkyl, hydroxy ($C_1$–$C_6$)alkyl, mercapto($C_1$–$C_6$)alkyl or carboxy ($C_1$–$C_6$)alkyl wherein the amino-, hydroxy-, mercapto- or carboxyl-group are optionally protected or the carboxyl-group amidated;
 lower alkyl substituted by carbamoyl, mono($C_1$–$C_6$ alkyl) carbamoyl, di($C_1$–$C_6$ alkyl)carbamoyl, di-($C_1$–$C_6$ alkyl)amino, or carboxy-$C_1$–$C_6$ alkanoylamino; or
 a cycloalkyl, cycloalkenyl or non-aromatic heterocyclic ring containing up to 3 heteroatoms, any of which may be (i) substituted by one or more substituents selected from $C_1$–$C_6$ alkyl, $C_2$–$C_6$ alkenyl, halo, cyano (—CN), —$CO_2H$, —$CO_2R$, —$CONH_2$, —CONHR, —$CON(R)_2$, —OH, —OR, oxo-, —SH, —SR, —NHCOR, and —$NHCO_2R^A$ wherein $R^A$ is $C_1$–$C_6$ alkyl or benzyl and/or (ii) fused to a cycloalkyl or heterocyclic ring;

$R_2$ is a $C_1$–$C_{12}$ alkyl,
 $C_2$–$C_{12}$ alkenyl,
 $C_2$–$C_{12}$ alkynyl,
 phenyl($C_1$–$C_6$ alkyl)-,
 heteroaryl($C_1$–$C_6$ alkyl)-,
 phenyl($C_2$–$C_6$ alkenyl)-,
 heteroaryl($C_2$–$C_6$ alkenyl)-,
 phenyl($C_2$–$C_6$ alkynyl)-,
 heteroaryl($C_2$–$C_6$ alkynyl)-,
 cycloalkyl($C_1$–$C_6$ alkyl)-,
 cycloalkyl($C_2$–$C_6$ alkenyl)-,
 cycloalkyl($C_2$–$C_6$ alkynyl)-,
 cycloalkenyl($C_1$–$C_6$ alkyl)-,
 cycloalkenyl($C_2$–$C_6$ alkenyl)-,
 cycloalkenyl($C_2$–$C_6$ alkynyl)-,
 phenyl($C_1$–$C_6$ alkyl)O($C_1$–$C_6$ alkyl)-, or
 heteroaryl($C_1$–$C_6$ alkyl)O($C_1$–$C_6$ alkyl)- group,
 any one of which may be optionally substituted by
 $C_1$–$C_6$ alkyl,
 $C_1$–$C_6$ alkoxy, halo, cyano (—CN), phenyl or heteroaryl, or phenyl or heteroaryl substituted by $C_1$–$C_6$ alkyl, $C_1$–$C_6$ alkoxy, halo, or cyano (—CN);

$R_3$ is selected from the group consisting of $C_1$–$C_6$ alkyl, phenyl, 2,- 3-, and 4-hydroxyphenyl, 2,- 3-, and 4-methoxyphenyl, 2- and 3-thienyl, 2,- 3-, and 4-pyridylmethyl, benzyl, 2,- 3-, and 4-hydroxybenzyl, 2,- 3-, and 4-benzyloxybenzyl, 2,- 3-, and 4-$C_1$–$C_6$ alkoxybenzyl, benzyloxy($C_1$–$C_6$alkyl)-, a group -(Alk) $_nR_6$ where Alk is a ($C_1$–$C_6$)alkyl or ($C_2$–$C_6$)alkenyl group, optionally interrupted by one or more —O—, —S— atoms or —N($R_7$)- groups, where $R_7$ is a hydrogen atom or a ($C_1$–$C_6$)alkyl group, n is 0 or 1, and $R_6$ is an optionally substituted cycloalkyl or cycloalkenyl group, a benzyl group substituted in the phenyl ring by a group of formula —$OCH_2COR_8$ where $R_8$ is hydroxyl, amino, ($C_1$–$C_6$)alkoxy, phenyl($C_1$–$C_6$) alkoxy, ($C_1$–$C_6$)alkylamino, di(($C_1$–$C_6$)alkyl)amino, phenyl($C_1$–$C_6$)alkylamino, the residue of an amino acid or acid halide, ester or amide derivative thereof, said residue being linked via an amide bond, said amino acid being selected from the group consisting of glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid, a heterocyclic($C_1$–$C_6$)alkyl group, either being unsubstituted or mono- or di-substituted in the heterocyclic ring with halo, nitro, carboxy, ($C_1$–$C_6$)alkoxy, cyano, ($C_1$–$C_6$)alkanoyl, trifluoromethyl ($C_1$–$C_6$)alkyl, hydroxy, formyl, amino, ($C_1$–$C_6$)alkylamino, di-($C_1$–$C_6$)alkylamino, mercapto, ($C_1$–$C_6$)alkylthio, hydroxy($C_1$–$C_6$)alkyl, mercapto($C_1$–$C_6$)alkyl or ($C_1$–$C_6$)alkylphenylmethyl, and a group-$CR_aR_bR_c$ in which:

each of $R_a$, $R_b$ and $R_c$ is independently hydrogen, ($C_1$–$C_6$)alkyl, ($C_2$–$C_6$)alkenyl, ($C_2$–$C_6$)alkynyl, phenyl($C_1$–$C_6$)alkyl, ($C_3$–$C_8$)cycloalkyl; or $R_c$ is hydrogen and $R_a$ and $R_b$ are independently phenyl or heteroaryl; or $R_c$ is hydrogen, ($C_1$–$C_6$)alkyl, ($C_2$–$C_6$)alkenyl, ($C_2$–$C_6$)alkynyl, phenyl($C_1$–$C_6$)alkyl, or ($C_3$–$C_8$)cycloalkyl, and $R_a$ and $R_b$ together with the carbon atom to which they are attached form a 3 to 8 membered cycloalkyl or a 5- to 6-membered heterocyclic ring; or $R_a$, $R_b$ and $R_c$ together with the carbon atom to which they are attached form a tricyclic ring; or $R_a$ and $R_b$ are each independently ($C_1$–$C_6$)alkyl, ($C_2$–$C_6$)alkenyl, ($C_2$–$C_6$)alkynyl, phenyl($C_1$–$C_6$)alkyl, or a group as defined for $R_c$ below other than hydrogen, or $R_a$ and $R_b$ together with the carbon atom to which they are attached form a cycloalkyl or heterocyclic ring, and $R_c$ is hydrogen, —OH, —SH, halogen, —CN, —$CO_2$H, ($C_1$–$C_4$)perfluoroalkyl, —$CH_2$OH, —$CO_2$($C_1$–$C_6$)alkyl, —O($C_1$–$C_6$)alkyl, —O($C_2$–$C_6$)alkenyl, —S($C_1$–$C_6$)alkyl, —SO($C_1$–$C_6$)alkyl, —$SO_2$($C_1$–$C_6$) alkyl, —S($C_2$–$C_6$)alkenyl, —SO($C_2$–$C_6$)alkenyl, —$SO_2$($C_2$–$C_6$)alkenyl or a group -Q-W wherein Q represents a bond or —O—, —S—, —SO— or —$SO_2$- and W represents a phenyl, phenylalkyl, ($C_3$–$C_8$) cycloalkyl, ($C_3$–$C_8$)cycloalkylalkyl, ($C_4$–$C_8$) cycloalkenyl, ($C_4$–$C_8$)cycloalkenylalkyl, heteroaryl or heteroarylalkyl group, which group W may optionally be substituted by one or more substituents independently selected from, hydroxyl, halogen, —CN, —$CO_2$H, —$CO_2$($C_1$–$C_6$)alkyl, —$CONH_2$, —CONH ($C_1$–$C_6$)alkyl, —CONH($C_1$–$C_6$alkyl)$_2$, —CHO, —$CH_2$OH, ($C_1$–$C_4$)perfluoroalkyl, —O($C_1$–$C_6$)alkyl, —S($C_1$–$C_6$)alkyl, —SO($C_1$–$C_6$)alkyl, —$SO_2$($C_1$–$C_6$) alkyl, —$NO_2$, —$NH_2$, —NH($C_{1-6}$)alkyl, —N(($C_1$–$C_6$) alkyl)$_2$, —NHCO($C_1$–$C_6$)alkyl, ($C_1$–$C_6$)alkyl, ($C_2$–$C_6$) alkenyl, ($C_2$–$C_6$)alkynyl, ($C_3$–$C_8$)cycloalkyl, ($C_4$–$C_8$) cycloalkenyl, phenyl or benzyl; and $R_4$ is an ester or thioester group.

2. A method as claimed in claim 1 wherein the stereochemical configuration of the carbon atom carrying the group $R_2$ is R, and that of the carbon atom carrying the groups $R_3$ and $R_4$ is S.

3. A method as claimed in claim 1 wherein $R_1$ is:

hydrogen, methyl, ethyl, n-propyl, n-butyl, isobutyl, hydroxyl, methoxy, allyl, phenylpropyl, phenylprop-2-enyl, thienylsulphanylmethyl, thienylsulphinylmethyl, or thienylsulphonylmethyl; or $C_1$–$C_4$ alkyl, eg methyl, ethyl n-propyl or n-butyl, substituted by a phthalimido, 1,2-dimethyl-3,5-dioxo-1,2,4-triazolidin-4-yl, 3-methyl-2,5-dioxo-1-imidazolidinyl, 3,4,4-trimethyl-2,5-dioxo-1-imidazolidinyl, 2-methyl-3,5-dioxo-1,2,4-oxadiazol-4-yl, 3-methyl-2,4,5-trioxo-1-imidazolidinyl, 2,5-dioxo-3-phenyl-1-imidazolidinyl, 2-oxo-1-pyrrolidinyl, 2,5-dioxo-1-pyrrolidinyl or 2,6-dioxopiperidinyl, 5,5-dimethyl-2,4-dioxo-3-oxazolidinyl, hexahydro-1,3-dioxopyrazolo[1,2,a][1,2,4]-triazol-2-yl, or a naphththalimido (ie 1,3-dihydro-1,3-dioxo-2H-benz[f]isoindol-2-yl), 1,3-dihydro-1-oxo-2H-benz[f]isoindol-2-yl, 1,3-dihydro-1,3-dioxo-2H-pyrrolo[3,4-b]quinolin-2-yl, or 2,3-dihydro-1,3-dioxo-1H-benz[d,e]isoquinolin-2-yl group; or cyclohexyl, cyclooctyl, cycloheptyl, cyclopentyl, cyclobutyl, cyclopropyl, tetrahydropyranyl or morpholinyl.

4. A method as claimed in claim 1 wherein $R_1$ is n-propyl, allyl, hydroxy, methoxy and thienylsulfanylmethyl.

5. A method as claimed in claim 1 wherein $R_2$ is:

$C_1$–$C_{12}$ alkyl, $C_3$–$C_6$ alkenyl or $C_3$–$C_6$ alkynyl;

phenyl($C_1$–$C_6$ alkyl)-, phenyl($C_3$–$C_6$ alkenyl)- or phenyl ($C_3$–$C_6$ alkynyl)- optionally substituted in the phenyl ring;

heteroaryl($C_1$–$C_6$ alkyl)-, heteroaryl($C_3$–$C_6$ alkenyl)- or heteroaryl(C3–$C_6$ alkynyl)- optionally substituted in the heteroaryl ring;

4-phenylphenyl($C_1$–$C_6$ alkyl)-, 4-phenylphenyl($C_3$–$C_6$ alkenyl)-, 4-phenylphenyl($C_3$–$C_6$ alkynyl)-, 4-heteroarylphenyl($C_1$–$C_6$ alkyl)-, 4-heteroarylphenyl ($C_3$–$C_6$ alkenyl)-, 4-heteroarylphenyl($C_3$–$C_6$ alkynyl)-, optionally substituted in the terminal phenyl or heteroaryl ring; or phenoxy($C_1$–$C_6$ alkyl)- or heteroaryloxy($C_1$–$C_6$ alkyl)- optionally substituted in the phenyl or heteroaryl ring.

6. A method as claimed in claim 1 wherein $R_2$ is: methyl, ethyl, n- or iso-propyl, n-, iso- or tert-butyl, n-pentyl, n-hexyl, n-heptyl, n-nonyl, n-decyl, prop-2-yn-1-yl, 3-phenylprop-2-yn-1-yl, 3-(2-chlorophenyl)prop-2-yn-1-yl, phenylpropyl, 4-chlorophenylpropyl, 4-methylphenylpropyl, 4-methoxyphenylpropyl, phenoxybutyl, 3-(4-pyridylphenyl)propyl-, 3-(4-(4-pyridyl) phenyl)prop-2-yn-1-yl, 3-(4-phenylphenyl)propyl-, 3-(4-phenyl)phenyl)prop-2-yn-1-yl, or 3-[(4-chlorophenyl) phenyl]propyl-.

7. A method as claimed in claim 1 wherein $R_2$ is isobutyl, n-hexyl, cyclopentylmethyl, benzyl, and 3-(2-chlorophenyl) prop-2-yn-1-yl.

8. A method as claimed in claim 1 wherein $R_3$ is phenyl, benzyl, tert-butoxymethyl or iso-butyl.

9. A method as claimed in claim 1 wherein $R_4$ is a group of formula —(C=O)$OR_9$, —(C=O)$SR_9$, —(C=S)$SR_9$, and —(C=S)$OR_9$ wherein $R_9$ is ($C_1$–$C_6$)alkyl, ($C_2$–$C_6$) alkenyl, cycloalkyl, cycloalkyl($C_1$–$C_6$)alkyl-, phenyl, heterocyclyl, phenyl($C_1$–$C_6$)alkyl-, heterocyclyl($C_1$–$C_6$) alkyl-, ($C_1$–$C_6$)alkoxy($C_1$–$C_6$)alkyl-, or ($C_1$–$C_6$)alkoxy ($C_1$–$C_6$)alkoxy($C_1$–$C_6$)alkyl-, any of which may be substituted on a ring or non-ring carbon atom or on a ring heteroatom, if present.

10. A method as claimed in claim 1 wherein $R_4$ is a group of formula —(C=O)$OR_9$ wherein $R_9$ is methyl, ethyl, n-or iso-propyl, n-, sec- or tert-butyl, 1-ethyl-prop-1-yl, 1-methyl-prop-1-yl, 1-methyl-but-1-yl, cyclopentyl, cyclohexyl, allyl, phenyl, benzyl, 2-, 3- and 4-pyridylmethyl, N-methylpiperidin-4-yl, 1-methylcyclopent-1yl, adamantyl, tetrahydrofuran-3-yl or methoxyethyl.

11. A method as claimed in claim 1 wherein $R_4$ is a group of formula —(C=O)$OR_9$ wherein $R_9$ is benzyl, cyclopentyl, isopropyl or tert-butyl.

12. A method as claimed in claim 1 wherein R is hydrogen or methyl.

13. A method as claimed in claim 1 wherein $R_1$ is n-propyl, allyl, hydroxy, methoxy or thienylsulfanyl-methyl, $R_2$ is isobutyl, n-hexyl, cyclopentylmethyl, benzyl or 3-(2-chlorophenyl)prop-2-yn-1-yl, $R_3$ is phenyl, benzyl, tert-butoxymethyl or iso-butyl, $R_4$ is a group of formula —(C=O)$OR_9$ wherein $R_9$ is benzyl, cyclopentyl, isopropyl or tert-butyl and R is hydrogen or methyl.

14. A method as claimed in claim 1 wherein the compound of formula (I) is 2S-(3S-hydroxycarbamoyl-2R-isobutyl-hex-5-enoylamino)-3-phenylpropionic acid cyclopentyl ester, or a pharmaceutically acceptable salt, hydrate or ester thereof.

15. A method according to claim 1 wherein the disease to be treated is asthma, rheumatoid arthritis, osteoarthritis, ulcerative colitis, contact and atopic dermatitis, psoriasis, multiple sclerosis, inflammatory bowel disease or Crohn's disease.

* * * * *